US005364343A

United States Patent [19]
Apolet et al.

[11] Patent Number: 5,364,343
[45] Date of Patent: Nov. 15, 1994

[54] IRRIGATION DEVICE FOR USE IN EAR CANALS FOR THERAPEUTIC OR HYGIENIC PURPOSES

[75] Inventors: Josef Apolet, Milan; Romano Ballotta, Soragna; Giovanni Cavallo, Acqui Terme, all of Italy

[73] Assignee: D.D. S.R.L., Milan, Italy

[21] Appl. No.: 983,317

[22] Filed: Nov. 30, 1992

Related U.S. Application Data

[63] Continuation-in-part of Ser. No. 844,858, Mar. 3, 1992, abandoned.

[30] Foreign Application Priority Data

Mar. 6, 1991 [IT] Italy .......... MI91 A 000582

[51] Int. Cl.⁵ .......... A61M 3/00
[52] U.S. Cl. .......... 604/43; 604/35; 604/36; 604/37; 239/124
[58] Field of Search .......... 604/27, 35, 36, 37, 604/39, 43; 239/124, 461

[56] References Cited

U.S. PATENT DOCUMENTS

| 694,541 | 3/1902 | Gordon | 604/39 |
|---|---|---|---|
| 1,779,268 | 10/1930 | Belfrage et al. | 604/39 |
| 1,845,343 | 2/1932 | Salerni | 604/39 X |
| 2,421,294 | 5/1947 | Shotton | |
| 2,494,088 | 1/1950 | Dulity | |
| 2,576,766 | 11/1951 | Sokolik | 604/39 X |
| 2,879,768 | 3/1959 | Anderson | 604/39 |
| 3,771,552 | 11/1973 | Waysilk et al. | |
| 4,206,756 | 6/1980 | Grossan | 604/39 |

FOREIGN PATENT DOCUMENTS

| 399288 | 6/1909 | France | |
| 28097 | 7/1884 | Germany | 604/39 |
| 16473 | of 1893 | United Kingdom | 604/39 |
| 23927 | of 1893 | United Kingdom | 604/39 |

*Primary Examiner*—Randall L. Green
*Assistant Examiner*—Mary Beth Jones
*Attorney, Agent, or Firm*—Oliff & Berridge

[57] ABSTRACT

An irrigation device for use in an ear canal is a main body of substantially conical shape having a central axis. There is at least one input duct connecting to a lavage liquid delivery apparatus for injecting the lavage liquid into the ear canal. There is at least one output duct allowing the continuous drainage of used lavage liquid. At least a part of the input duct has an axis which is inclined relative to the central axis of the main body. This directs impingement of the lavage liquid against wall surfaces and not against the eardrum.

6 Claims, 2 Drawing Sheets

IRRIGATION DEVICE FOR USE IN EAR CANALS FOR THERAPEUTIC OR HYGIENIC PURPOSES

This is a continuation-in-part of application Ser. No. 07/844,858, filed Mar. 3, 1992, now abandoned.

The present invention relates to an irrigation device suitable for the introduction of a lavage liquid, for hygienic or therapeutic purposes, in the ear canals and at the same time for the drainage of the used liquid.

PRIOR ART

It is known that, in case of particular affections of internal organs, such as the ear canal, the intestinal tract, vagina etc. medicaments have to be administered in the form of solutions for irrigation and that, also for a common preventive and hygiene praxis, the lavage of said internal parts should be performed regularly.

The instruments normally employed, continuous suppliers such as by phleboclysis, syringes or other plunger instruments, rubber syringes, etc. normally have a container in which is contained, or is taken in at the time of use, the liquid to be employed, which is then administered through a suitable duct.

Obviously, with devices of that type it is necessary to repeatedly stop the lavage operations in order to allow the aspiration, or in general the outpouring of the introduced liquid from the canal which is being washed. This is evidently inconvenient for the operator and requires for the patient the presence of specialised personnel in order that the operation be safely performed.

A jet ear irrigation system (U.S. Pat. No. 4,206,756; M. Grossan) is well known in the art. In this device the flow is supplied to the ear by means of an applicator having a tapered end which ends in a smooth convex manner. The tube connects by a male connector to a standard female counterpart, using a pulsating dental irrigation device. At the distal end, three holes are present. The position of the three openings provides for a pulsating solution to eject through two holes on one side and one hole on the opposite side. However, in this device no output ducts are provided and the pulsating jets (preferably 1000 cycles per minute or somewhat higher) disturb the patient.

DETAILED DESCRIPTION OF THE INVENTION

The present invention obviates the mentioned drawbacks by means of an irrigation device to be applied to the liquid supplying apparatus, and in which at least one outlet duct is provided allowing the continous drainage of the used lavage liquid, thus permitting the dressing and/or lavaging operations of the ear canals in a continuous and safe way.

The invention will now be described with reference to the attached FIGS. 1-3, which are shown only for illustrative, purposes.

Figure 1:
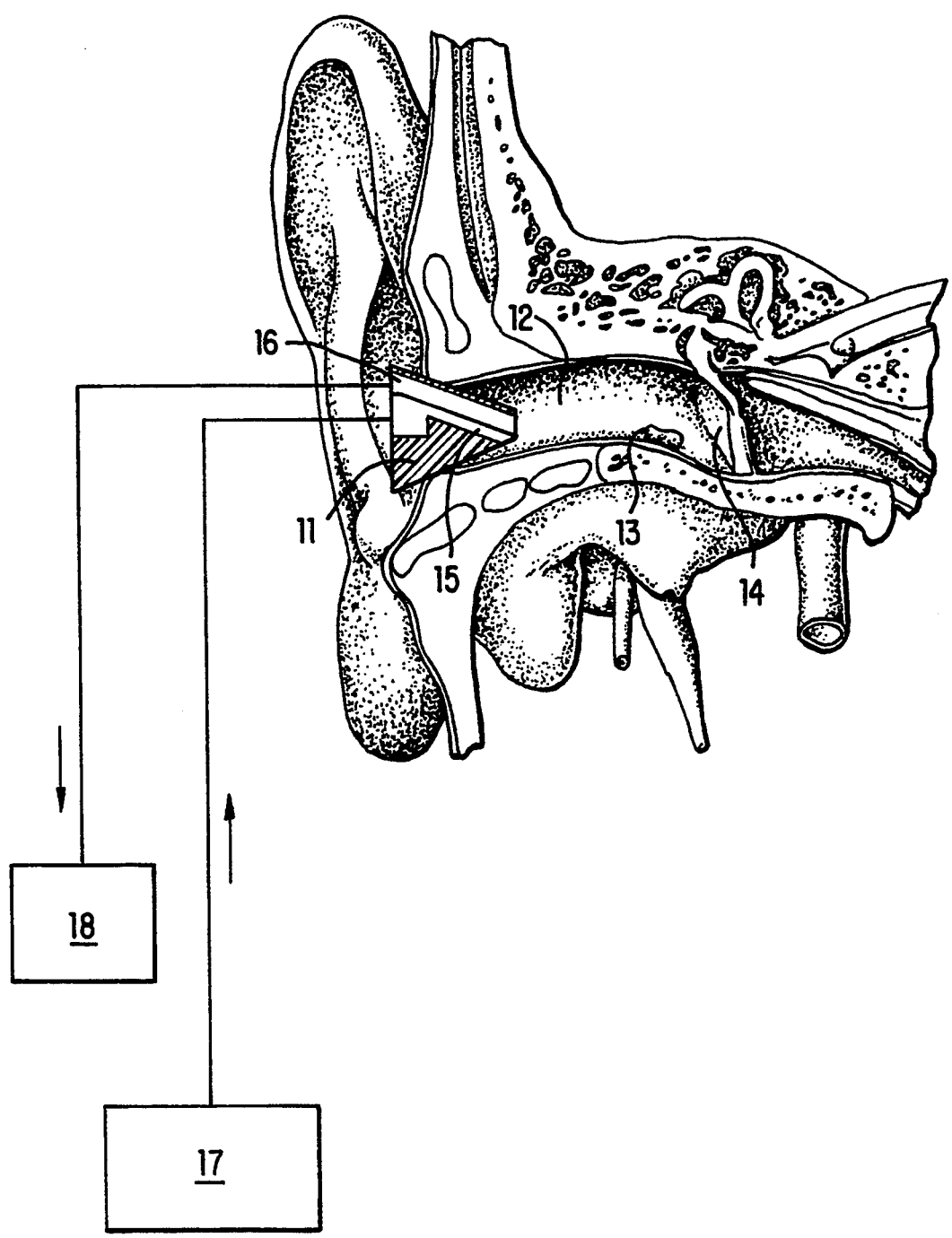
FIG. 1 is an enlarged sectional view of the ear of a person with a first embodiment of the irrigation device according to the present invention.

FIG. 1 shows a first embodiment of the irrigation device 11 situated in the correct position within the ear canal 12. 13 indicates a typical particle of cerumen blocking hearing because it blocks the passage of sound to the eardrum 14. The eardrum 14 and the organs behind it are delicate, and it is suitable to be extremely gentle in order not to cause dammage. The eardrum 14 is very thin and is very fragile, and can be damaged if excessive force is used. As shown in FIG. 1, the irrigation device 11 consists essentially of one inlet duct 15 and one outlet duct 16. Said inlet duct 15 is connected to the liquid delivery apparatus 17, whereas said outlet duct 16 is connected with an aspiration apparatus 18 for analysis or other purposes of the used output liquid.

Figure 2:
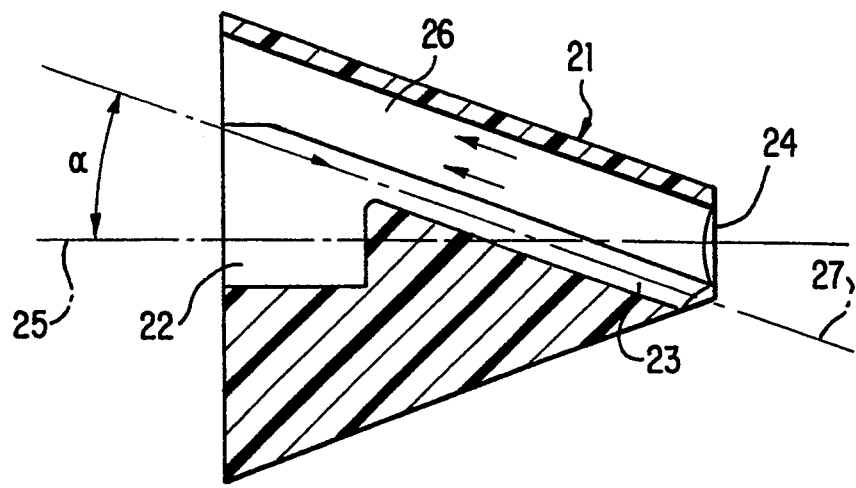
FIG. 2 represents an enlarged section of the first embodiment shown in FIG. 1.

As shown in FIG. 2, the first embodiment of the device according to the invention, already represented in FIG. 1, consists in a main body 21 of essentially conical shape apt to be applied to the ear canal 12 (FIG. 1), corresponding to the canal through which the lavage operation is to be performed.

According to this first embodiment of the invention, the main body 21 may be made to adapt to the shape of the person's ear, following the techniques commonly employed for taking the auricular prints (as it is done for instance when adapting to the ear devices for improving the hearing). The input and output ducts are then adapted to the device as will be described further below.

Said main body 21 comprises a cavity 22 suitably shaped for connection (screwing, pressure, release connections, etc.) of the device to the liquid delivery apparatus 17 (FIG. 1). From the cavity 22, an inlet duct 23 goes through the main body 21 reaching the distal end 24 opposite to the cavity 22. The inlet duct 23 is suitably shaped so that the injected liquid is deviated with respect to the central axis 25 of the main body 21. The angle $\alpha$ between the central axis 25 and the axis 27 of said inlet duct 23 comprises an angle between 20° and 70°.

In this way the injected liquid is projected against the wall surfaces of the ear canal 12 (FIG. 1) rather than directly against the eardrum 14 (FIG. 1). This avoids exerting a pressure, which may be damaging, directly or internal organs. In particular in this way, the possible labyrinth stimulation which is responsible of headaches and/or dizziness is avoided.

The inlet duct 23 may have any shape, but preferably a cylindrical one.

An outlet duct 26 in the main body 21 allows the drainage of the used lavage liquid.

The outlet duct 26 may thus be an additional duct, completely independent of the inlet duct 23, or other similar arrangements may be foreseen.

According to a preferred embodiment, one may, for instance, foresee a single duct longitudinally divided by a separating wall into two parts through one of which flows the input liquid and through the other the used liquid discharged, or two co-axial ducts, one for the input liquid and the other for the output used liquid.

Figure 3:
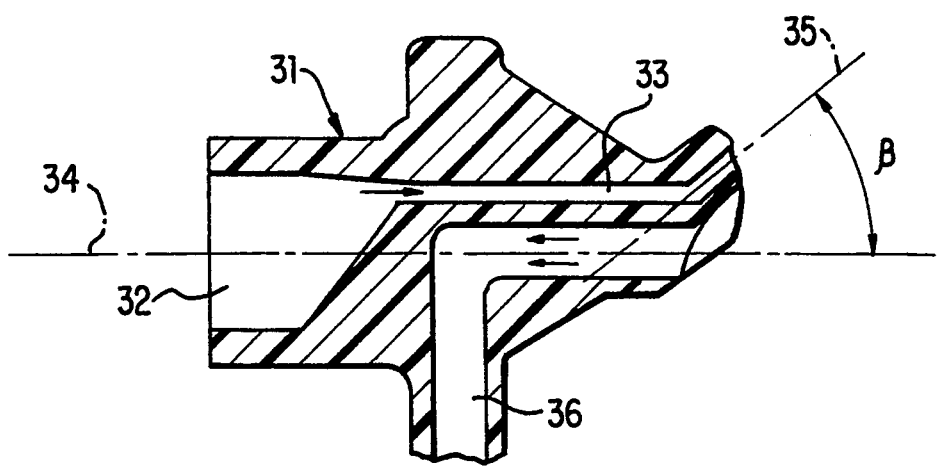
FIG. 3 represents an enlarged section of a second embodiment of the present invention.

FIG. 3 shows, in section, another possible embodiment. Others may be easily conceived by a person skilled in the art. In FIG. 3 the second embodiment consists in a main body 31 of a particular shape apt to be applied to the ear canal. Said main body 31 comprises a cavity 32 connected with an input duct 33, and an output duct 36 for the drainage of the used Liquid. The angle $\beta$ formed by the central axis 34 of the main body 31 and the axis 35 of the final portion of the input duct 33 is preferably between 20° and 70°.

The ratio between the section of the output ducts 16; 26; 36 and of the input ducts 15; 23; 33 should be 1:1 or higher in order to allow the free drainage of the used output liquid.

According to a particular embodiment of the invention, not represented in the FIGS. 1–3, the output duct at its distal end is consists of a nozzle with multiple holes, in order to avoid clogging during the operation of drainage of the used liquid.

The different elements of the device, according to the invention, may be made out of any suitable substance.

Silicone and/or plastic materials are preferred, which allow a rapid and accurate cleaning and have an elasticity which permits adaption of the device to the particular ear canal.

Since the device, according to the present invention, is of simple use, it may be included in a kit for personal use, consisting of one or more containers for the lavage liquid and of one or more devices, according to the present invention, which could be thrown away after use.

The device according to the invention may also be connected to a suitable reservoir from which the liquid to be employed may be supplied by conventional means, e.g. plunger instruments or rubber syringes, etc.

We claim:

1. An irrigation device for use in an ear canal comprising:
a main body of substantially conical shape having a central axis and providing one duct divided by a separating wall into two parts, comprising a first irrigating part connecting to a lavage liquid delivery apparatus for the injection of said lavage liquid into said ear canal and a second drainage part allowing the continuous drainage of the used lavage liquid, wherein said input duct has an axis which is inclined relative to said central axis of said main body to direct impingement of said lavage liquid against wall surfaces of said ear canal without direct impingement of a stream against said eardrum.

2. An irrigation device according to claim 1, wherein said irrigating part and said drainage part extend in the same direction.

3. An irrigation device according to claim 1, wherein said irrigating part and said drainage part each have a cross-sectional area and wherein a ratio of said drainage part cross-sectional area to said irrigating part cross-sectional area is at least 1:1.

4. An irrigation device according to claim 1, wherein an angle formed by said central axis of said main body and by an axis of said at least a part of said irrigating part comprises an angle between 20° and 70°.

5. An irrigation device according to claim 1, wherein said main body is shaped to adapt to the particular conformation of said ear canal.

6. An irrigation device according to claim 1, wherein said main body consists of a member selected from the group consisting of plastic, silicon and mixtures thereof.

* * * * *